United States Patent [19]
Blom

[11] Patent Number: 5,571,180
[45] Date of Patent: *Nov. 5, 1996

[54] TOOL FOR LOADING FLEXIBLE FLANGE INTO RETAINER

[75] Inventor: Eric D. Blom, Indianapolis, Ind.

[73] Assignee: Hansa Medical Products, Inc., Indianapolis, Ind.

[*] Notice: The term of this patent shall not extend beyond the expiration date of Pat. No. 5,300,119.

[21] Appl. No.: 416,589

[22] Filed: Apr. 3, 1995

Related U.S. Application Data

[60] Continuation of Ser. No. 143,835, Oct. 27, 1993, abandoned, which is a division of Ser. No. 818,853, Jan. 10, 1992, Pat. No. 5,300,119.

[51] Int. Cl.$^6$ .................................................. A61F 2/20
[52] U.S. Cl. .................................. 623/9; 623/66; 604/11; 604/15
[58] Field of Search .......................... 604/11–18; 623/9, 623/66

[56] References Cited

U.S. PATENT DOCUMENTS

| | | | |
|---|---|---|---|
| 3,765,416 | 10/1973 | Werner et al. | 604/18 |
| 4,421,504 | 12/1983 | Kline | 604/18 X |
| 4,435,853 | 3/1984 | Blom et al. | 3/1.3 |
| 4,610,659 | 9/1986 | Friese | 604/11 |
| 4,614,516 | 9/1986 | Blom et al. | 623/9 |
| 4,676,773 | 6/1987 | Sheldon | 604/11 |
| 4,690,671 | 9/1987 | Coleman et al. | 604/15 |
| 4,695,275 | 9/1987 | Bruce et al. | 604/264 |
| 4,900,303 | 2/1990 | Lemelson | 604/11 X |
| 4,911,687 | 3/1990 | Stewart et al. | 604/11 X |
| 4,911,716 | 3/1990 | Blom et al. | 623/9 |
| 4,923,440 | 5/1990 | Genaro | 604/11 X |
| 4,964,850 | 10/1990 | Bouton et al. | 604/54 |
| 5,041,080 | 8/1991 | Shimatani et al. | 604/11 X |
| 5,108,421 | 4/1992 | Fowler | 604/15 |
| 5,300,119 | 4/1994 | Blom | 623/11 |

FOREIGN PATENT DOCUMENTS

0222509A3  5/1987  United Kingdom.

*Primary Examiner*—Paul B. Prebilic
*Attorney, Agent, or Firm*—Barnes & Thornburg

[57] ABSTRACT

A device for insertion into a puncture in a tracheoesophageal wall includes a cylindrical body and a flexible first flange provided on an outside surface of the body. The flange has a use orientation in which it projects generally outwardly from the outside surface of the body and an insertion orientation in which it is resiliently folded toward the axis of the body. A retainer constructed of a material soluble in fluids present in the tracheoesophageal wall and esophagus retains the flange in its resiliently folded orientation. A method for inserting the device into the puncture comprises the steps of resiliently deflecting the flange toward the axis of the body, placing the retainer over the resiliently folded flange, and either pushing the body, resiliently folded flange first, into the puncture so that the resiliently folded flange lies on the esophageal side of the tracheoesophageal wall, or pulling the body, resiliently folded flange first, into the puncture so that the resiliently folded flange lies on the tracheal side of the tracheoesophageal wall.

3 Claims, 6 Drawing Sheets

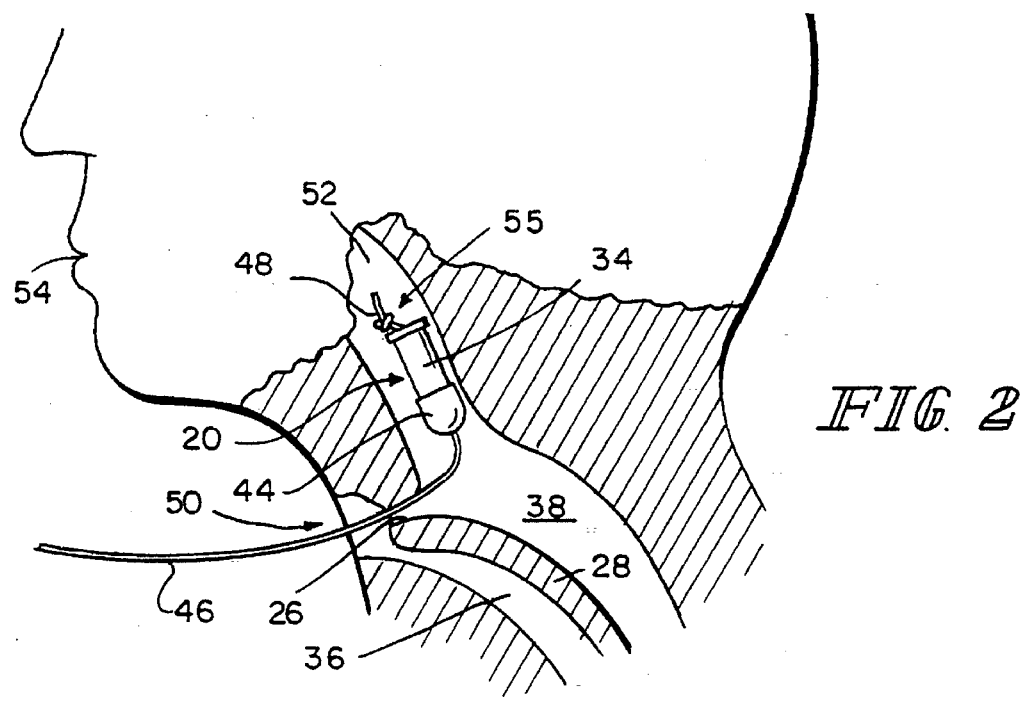
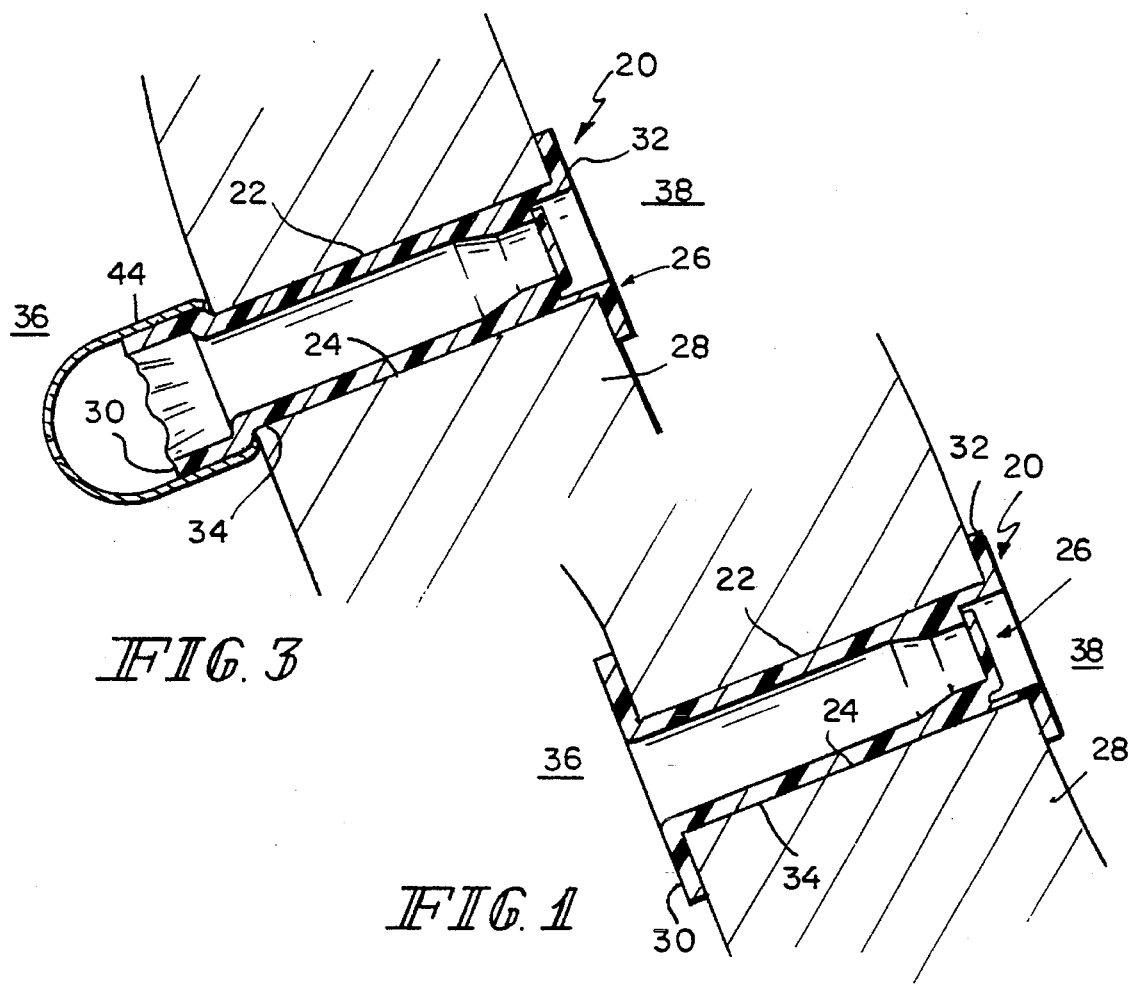

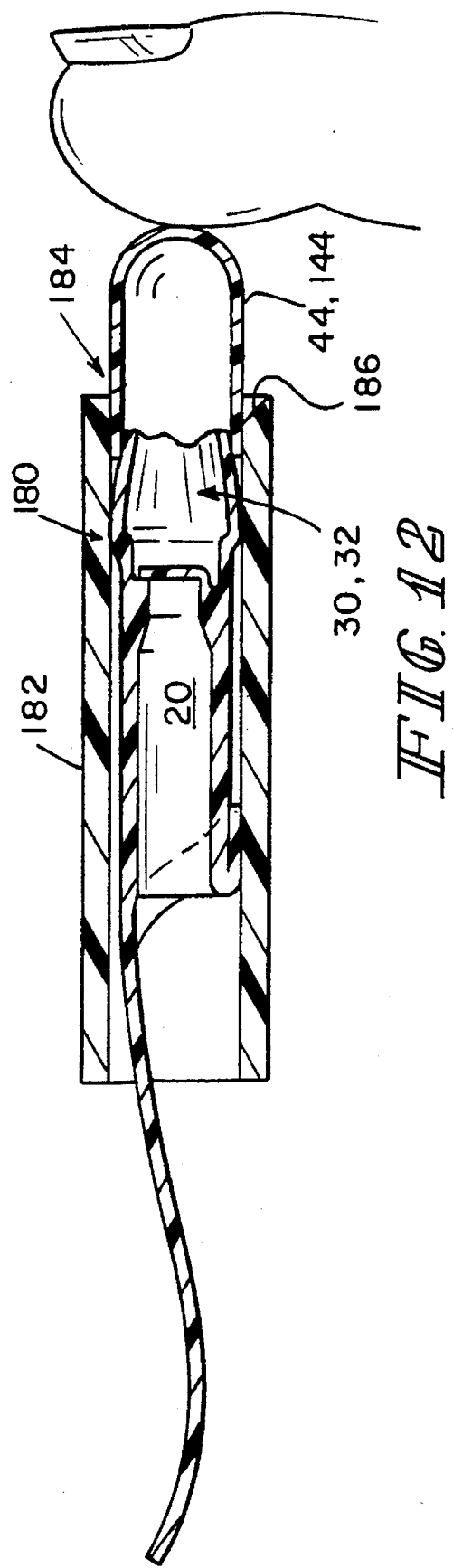
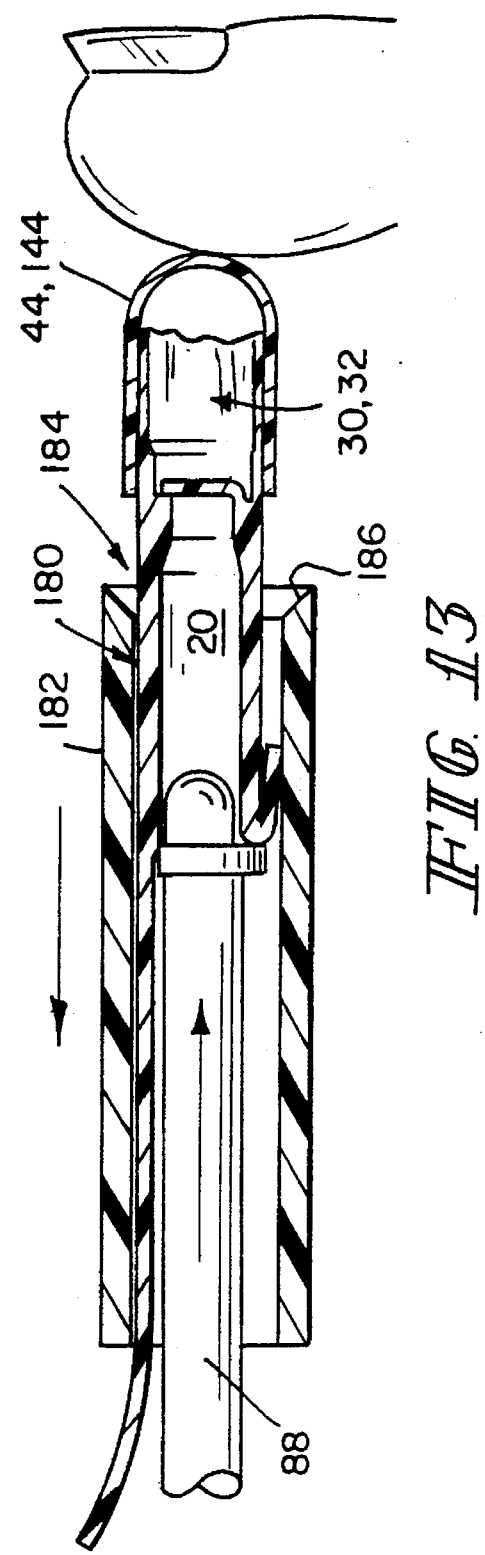

TOOL FOR LOADING FLEXIBLE FLANGE INTO RETAINER

This application is a continuation of application Ser. No. 08/143,835 filed Oct. 27, 1993, now abandoned, which is a divisional application of application Ser. No. 07/818,853 filed Jan. 10, 1992, now U.S. Pat. No. 5,300,119.

This invention relates to a method and apparatus for the delivery, or placement, of, for example, a voice prosthesis device into a puncture provided in the tracheoesophageal wall of a speech restoration patient.

A speech restoration technique is known wherein air from the trachea is diverted from its normal flow path out through the tracheostoma to a flow path through a voice prosthesis providing a more or less permanent passageway to the esophagus. Esophageal speech results. See U.S. Pat. Nos.: 4,435,853; 4,614,516; and 4,911,716. Voice prostheses currently in use for providing controlled air pathways through tracheoesophageal punctures incorporate flexible retention collars. The retention collar lies against the esophageal surface of the tracheoesophageal wall to reduce the likelihood of dislodgement of the prosthesis from the puncture. While this configuration substantially improves retention, the presence of the large retention collar makes insertion of a prosthesis more difficult and traumatic to the tissue surrounding the tracheoesophageal puncture. A possibility inherent in difficult or traumatic prosthesis insertion is incomplete insertion. Incomplete insertion may result in aspiration of the prosthesis into the airway. The prosthesis may be expelled by coughing, requiring endoscopic retrieval from the airway. Additionally, concern about prosthesis insertion difficulty may prevent some patients and physicians from employing this method of voice restoration.

According to an aspect of the invention, a retainer is provided for atraumatic insertion of a prosthesis into a puncture in the tracheoesophageal wall. The prosthesis includes a cylindrical body and a flexible first flange provided on an outside surface of the body. The flange has a use orientation in which it projects generally outwardly from the outside surface of the body and an insertion orientation in which it is resiliently folded toward the axis of the body. The retainer retains the flange in its resiliently folded orientation.

The retainer illustratively is constructed of a material soluble in fluids present in the tracheoesophageal wall and the esophagus.

Illustratively, the first flange is positioned adjacent a first end of the body which is inserted through the puncture.

Additionally, illustratively, the prosthesis further comprises a second flange spaced along the body from the first flange toward a second end of the body. Illustratively, the second flange is also a flexible flange.

According to another aspect of the invention, a method is provided for atraumatically inserting into a puncture in the tracheoesophageal wall a prosthesis including a cylindrical body and a flexible flange provided on an outside surface of the body. The flange has a use orientation in which it projects generally outwardly from the outside surface of the body. The method comprises the steps of resiliently deflecting the flange toward the axis of the body and placing over the resiliently folded flange a retainer.

Illustratively the retainer is constructed of a material soluble in fluids present in the tracheoesophageal wall and the esophagus.

Illustratively, the method further comprises the step of pushing the body, resiliently folded flange first, into the puncture so that the resiliently folded flange lies on the esophageal side of the tracheoesophageal wall.

Alternatively, the method further comprises the step of pulling the body, resiliently folded flange first, into the puncture so that the resiliently folded flange lies on the tracheal side of the tracheoesophageal wall.

The term "cylindrical body" as used herein, means a body including a surface generated by a straight line moving always parallel to another straight line in a closed path.

The invention may best be understood by referring to the following detailed description and accompanying drawings which illustrate the invention. In the drawings:

FIG. 1 illustrates a fragmentary sectional view through the tracheoesophageal wall of a wearer of a voice prosthesis device according to the present invention and longitudinally through the voice prosthesis device itself;

FIG. 2 illustrates a step in a method of insertion of the voice prosthesis device of FIG. 1 according to the invention;

FIG. 3 illustrates a further step in the method, a step of which is illustrated in FIG. 2;

FIG. 12–13 illustrate steps in a method of placement of a retainer onto a speech prosthesis according to the present invention.

Figure 5:
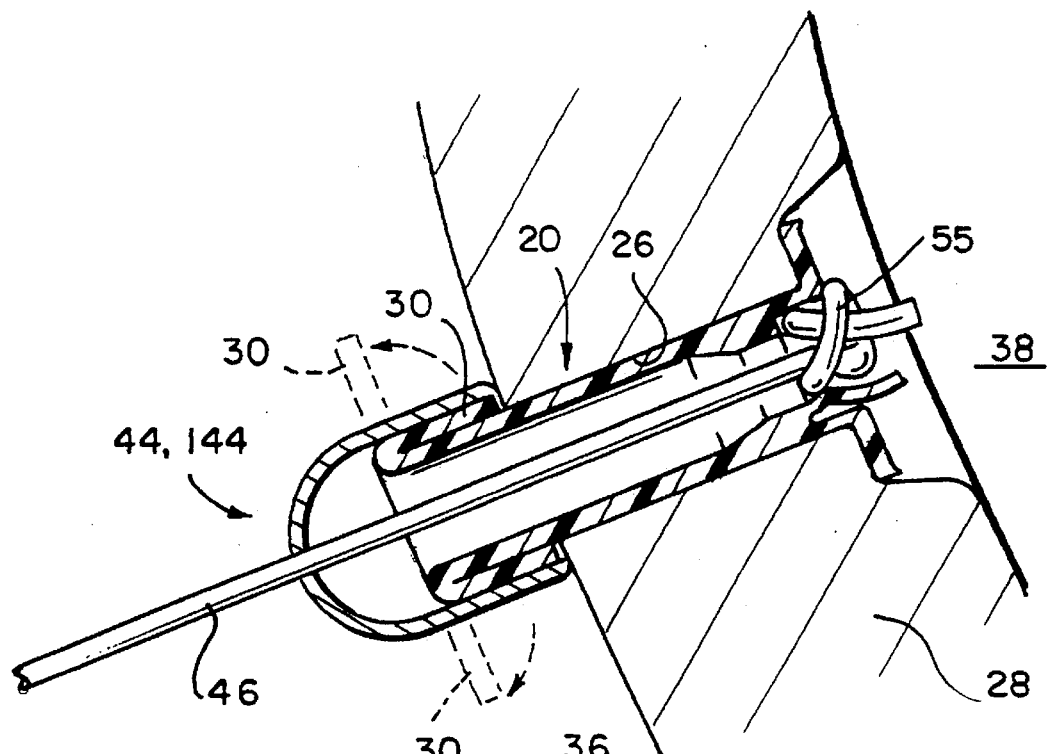
FIG. 5 illustrates a step in another method of insertion of the voice prosthesis device of FIG. 1 according to the invention.

Turning now to the drawings, a voice prosthesis device 20 includes a body 22 of a pliable silicone. The silicone must be rigid enough to withstand the forces placed upon it by the wall 24 of the puncture 26 through the tracheoesophageal wall 28 in which it resides. It must also be pliable enough to permit the folding of the retention flanges 30, 32 formed on its outside surface 34 adjacent its tracheal 36 and esophageal 38 ends, respectively. Flanges 30, 32 are responsible for positioning body 22 in the puncture 26 and reducing the likelihood of it being displaced in either the tracheal 36 or esophageal 38 direction.

Figure 6:
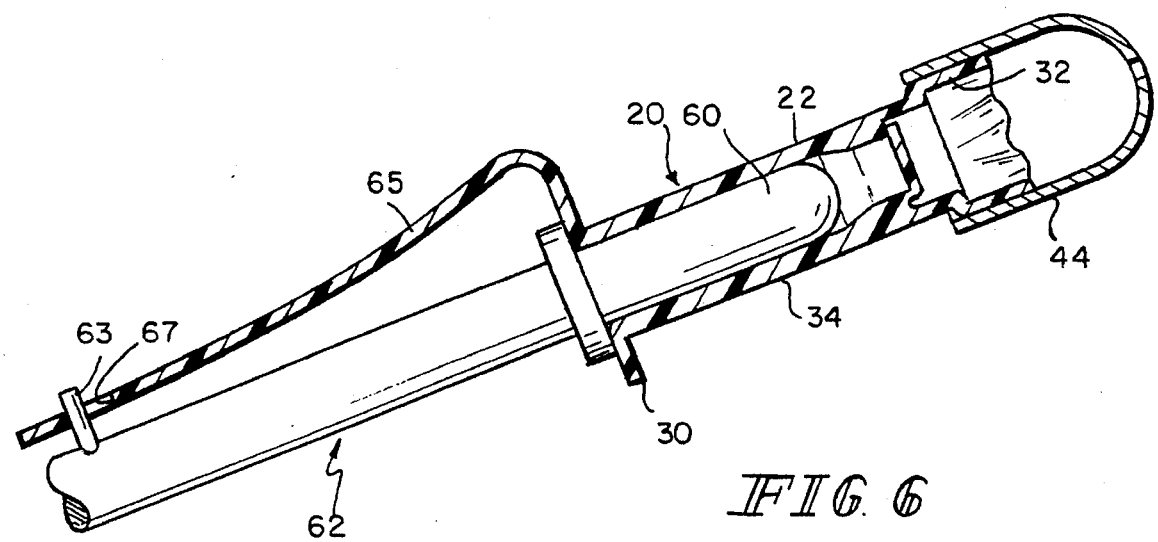
FIG. 6 illustrates a step in a method of insertion of the voice prosthesis device of FIG. 1 according to the invention.
Figure 7:
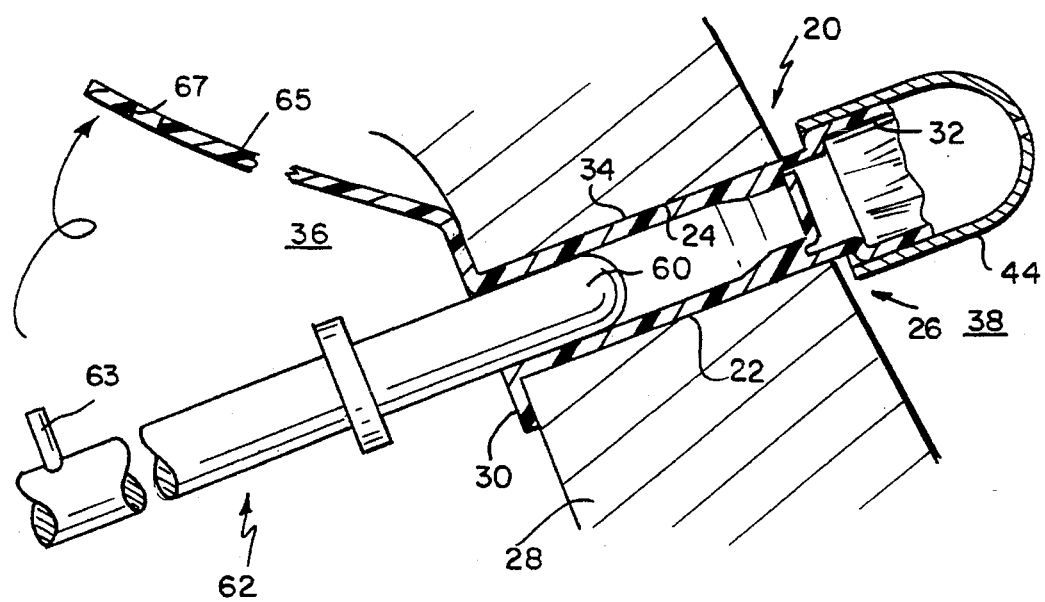
FIG. 7 illustrates a step in a method of insertion of the voice prosthesis device of FIG. 1 according to the invention.

Flanges 30, 32 are sufficiently flexible that they can be collapsed or folded into non-use, or insertion, orientations as illustrated by flange 30 in FIGS. 2–3 and flange 32 in FIGS. 6–7. Flanges 30, 32 are retained in these orientations by retainer 44 which illustratively may be cut-off portions of gelatin capsules. Once the voice prosthesis device 20 is inserted into the puncture 26, fluids such as saliva and the like, present in the tracheoesophageal wall 28 and the esophagus 38 dissolve the retainers 44 permitting the flanges 30, 32 to assume their use orientations illustrated in FIG. 1.

FIGS. 2 and 3 illustrate one method of delivery of a voice prosthesis 20 into a puncture 26. In this method, a pediatric catheter 46 (approximately French size 4), preferably, with a Cudétip, is threaded through the tracheostoma 50, puncture 26 and upward through the pharynx 52 and out through the mouth 54 of a patient. The voice prosthesis 20 with flange 30 captured by a retainer 44 in folded, or insertion, orientation, is then threaded onto the tip 48 of the catheter 46. The retainer 44 is provided with a hole 53 in the tip thereof through which catheter 46 is threaded. A knot 55 is tied in the tip 48 of the catheter 46 to capture prosthesis 20 thereon, and the catheter 46 is pulled back downward through the pharynx 52 and puncture 26. This properly locates voice prosthesis 20 with flange 32 in its deployed, use, orientation and flange 30 still captured in its folded, non-use orientation. However, as retainer 44 is exposed to secretions and the like in the esophagus 38 and tracheoesophageal wall 28, retainer 44 dissolves and flange 30 deploys to its use orientation, positioning prosthesis 20 in puncture 26. Of course, catheter 46 may be removed at any time once voice prosthesis 20 is in place in the puncture, but the clinician may choose to wait to remove catheter 46 until flange 30 is deployed. The catheter 46 is removed by threading it back up through the pharynx 52, out through the mouth 54, untying the knot 55, and then pulling the catheter 46 out through the tracheostoma 50.

Figure 4:
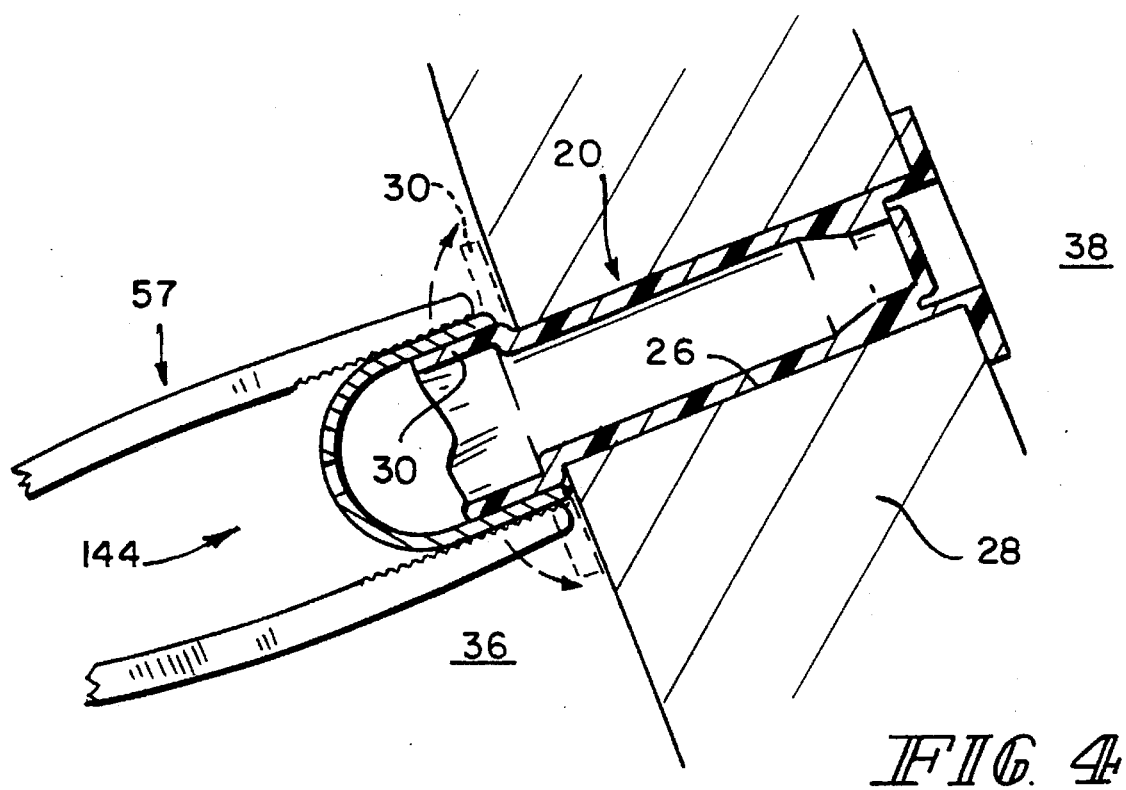
FIG. 4 illustrates a step in another method of insertion of the voice prosthesis device of FIG. 1 according to the invention.

Steps in two more insertion techniques are illustrated in FIGS. 4–5. In these techniques, a retainer 144 is employed which may or may not be soluble in fluids present in the tracheoesophageal wall and the esophagus. These methods work equally well in both cases. In these methods, the retainer 144 is placed over flange 30 to capture it in either forward folded (FIG. 4) or rearward folded (FIG. 5) orientation. The catheter 46 is located as in the embodiment of FIGS. 2–3 and the prosthesis 20 with retainer 144 thereon is threaded onto the catheter 46 and secured. The prosthesis is pulled downward through the pharynx 52 and located in the puncture 26. As illustrated in FIG. 4, the clinician then threads the catheter back up through the pharynx 52, unties the knot 55, and pulls the catheter 46 out. Finally, the clinician inserts a forceps, tweezers or the like 57 through the tracheostoma 50, removes the retainer 144 and pulls it out, deploying the flange 30 to its broken line position illustrated in FIG. 4.

A step in another technique for deploying flange 30 is illustrated in FIG. 5. In FIG. 5, flange 30 has been deflected rearwardly during the process of placing a retainer 44 or 144 on the leading end of prosthesis 20. As in the embodiment illustrated in FIG. 4, the catheter 46 is located as in the embodiment of FIGS. 2–3 and the prosthesis 20 with retainer 44 or 144 thereon is threaded onto the catheter 46 and secured. The prosthesis is then pulled downward through the pharynx 52 and into the puncture 26. However, instead of simply locating the prosthesis 20 correctly in the puncture 26, tension is maintained on catheter 46 sufficient to deflect the esophageal side 38 of the tracheoesophageal wall 28 toward the tracheal side 36 thereof. Then the retainer 44 is permitted to dissolve or the retainer 144 is removed as described in connection with FIG. 4, deploying flange 30 to its broken line orientation. Then the tension on catheter 46 is released, permitting prosthesis 20 to assume its proper orientation in puncture 26 and catheter 46 is removed, for example as described in connection with FIG. 4.

FIGS. 6 and 7 illustrate another method of delivery of a voice prosthesis 20 into a puncture 26. In this method, a retainer 44 is placed over flange 32, folding flange 32 into its non-use, or insertion, orientation. The voice prosthesis 20 is placed on the tip 60 of an insertion tool 62. Insertion tool 62 has a retainer peg 63. Voice prosthesis device 20 is provided with a strap 65 at its tracheal 36 end, illustratively formed on flange 30. Strap 65 is provided with an aperture 67 for accommodating peg 63 to retain prosthesis device 20 on tool 62 during insertion of device 20. Tool 62 is then manipulated through the tracheostoma (such as tracheostoma 50 in FIG. 2) of the wearer, and voice prosthesis 20 is inserted through the puncture 26. This properly locates voice prosthesis 20 with flange 30 in its deployed, or use, orientation and flange 32 still captured in its folded, non-use, orientation. However, as retainer 44 is exposed to saliva and the like on the esophageal 38 side of tracheoesophageal wall 28, retainer 44 dissolves and flange 32 deploys to its use orientation, positioning prosthesis 20 in puncture 26. Of course, tool 62 may be removed from prosthesis 20 at any time by removing strap 65 from peg 63, and then withdrawing tool 62. However, again, the clinician may choose to wait to remove tool 62 until flange 32 is deployed. Finally, since strap 65 is not needed once prosthesis 20 is inserted, strap 65 can be clipped from flange 30 and discarded.

Figure 8:
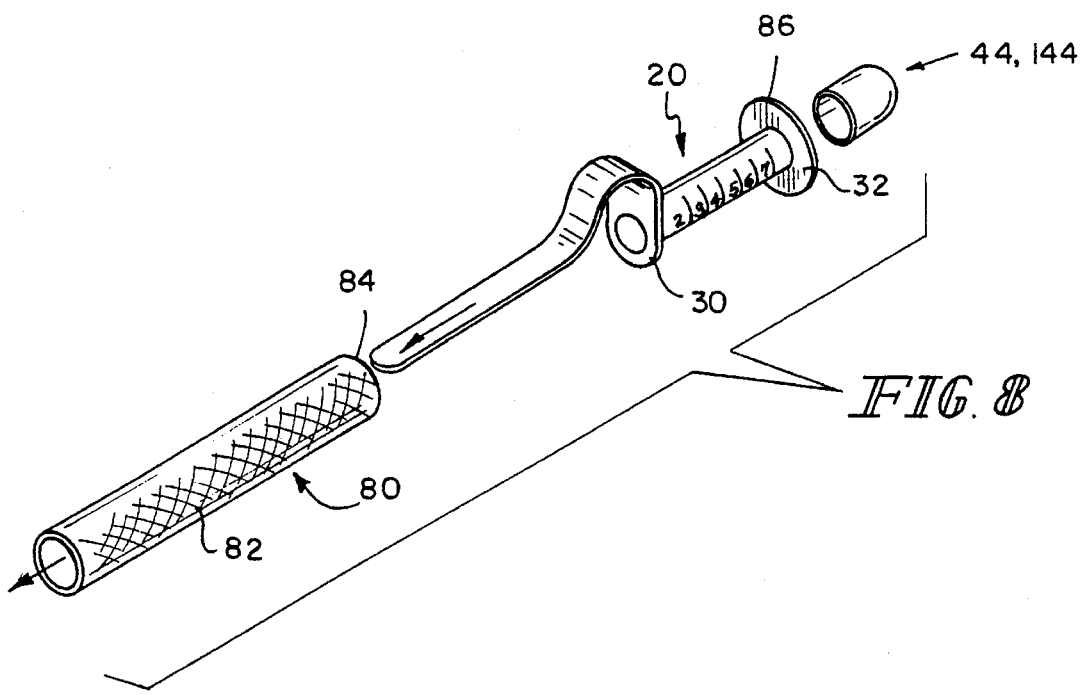
FIGS. 8–10 illustrate steps in a method of placement of a retainer onto a speech prosthesis according to the present invention.
Figure 9:
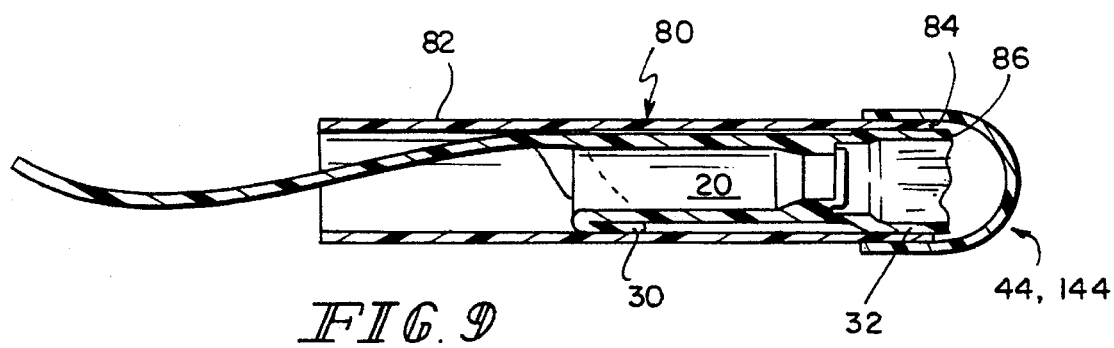
Figure 10:
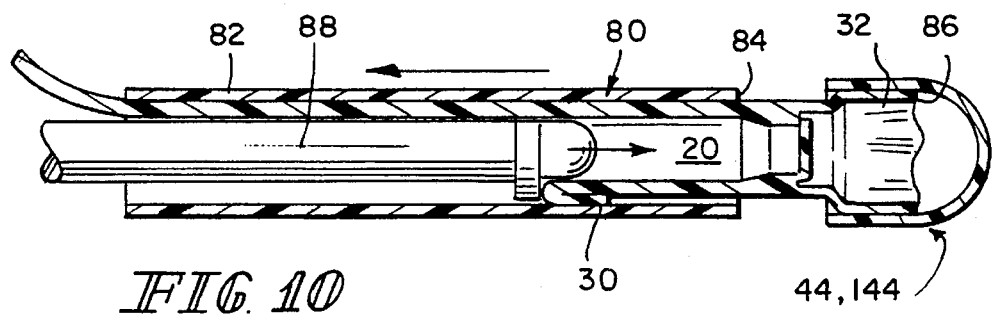

FIGS. 8–10 illustrate steps in the loading of a flange, whether it be flange 30 or 32, into a retainer 44 or 144, to the orientation illustrated in FIGS. 2–4, 6 and 7. In the first step in the method, illustrated in FIG. 8, the prosthesis 20 is inserted into a thin-walled tool, in this case, a tube 80 to the orientation illustrated in FIG. 9. The outer sidewall 82 of tube 80 illustratively is knurled or otherwise textured to aid in gripping of the tube 80 during the process. The tube 80 comprises a cylindrical passageway having a cross section slightly larger than the cross section of the cylindrical body 22 of the device but smaller than the flange 30 or 32. Once the prosthesis has reached the orientation illustrated in FIG. 9, the retainer 44 or 144 is placed over the end 84 of the tube 80 from which the edge 86 of the folded flange 30 or 32 projects slightly. Then, referring to FIG. 10, a tool 88 of somewhat the same general configuration as tool 62 is pushed through the open end of the tube 80, engages the open end of prosthesis 20 and pushes prosthesis 20 out of tube 80 carrying the retainer 44 or 144 with it to retain flange 30 or 32 in its folded orientation illustrated in FIGS. 2–4, 6–7, 9 and 10. The prosthesis 20 is then ready for insertion using one of the methods described in connection with FIGS. 2–4 and 6–7. To load a flange 30 or 32 to the orientation illustrated in FIG. 5, the retainer 44 or 144 is simply pushed on an end of the prosthesis 20 deflecting the flange 30 or 32 along the length of prosthesis 20.

Figure 11:
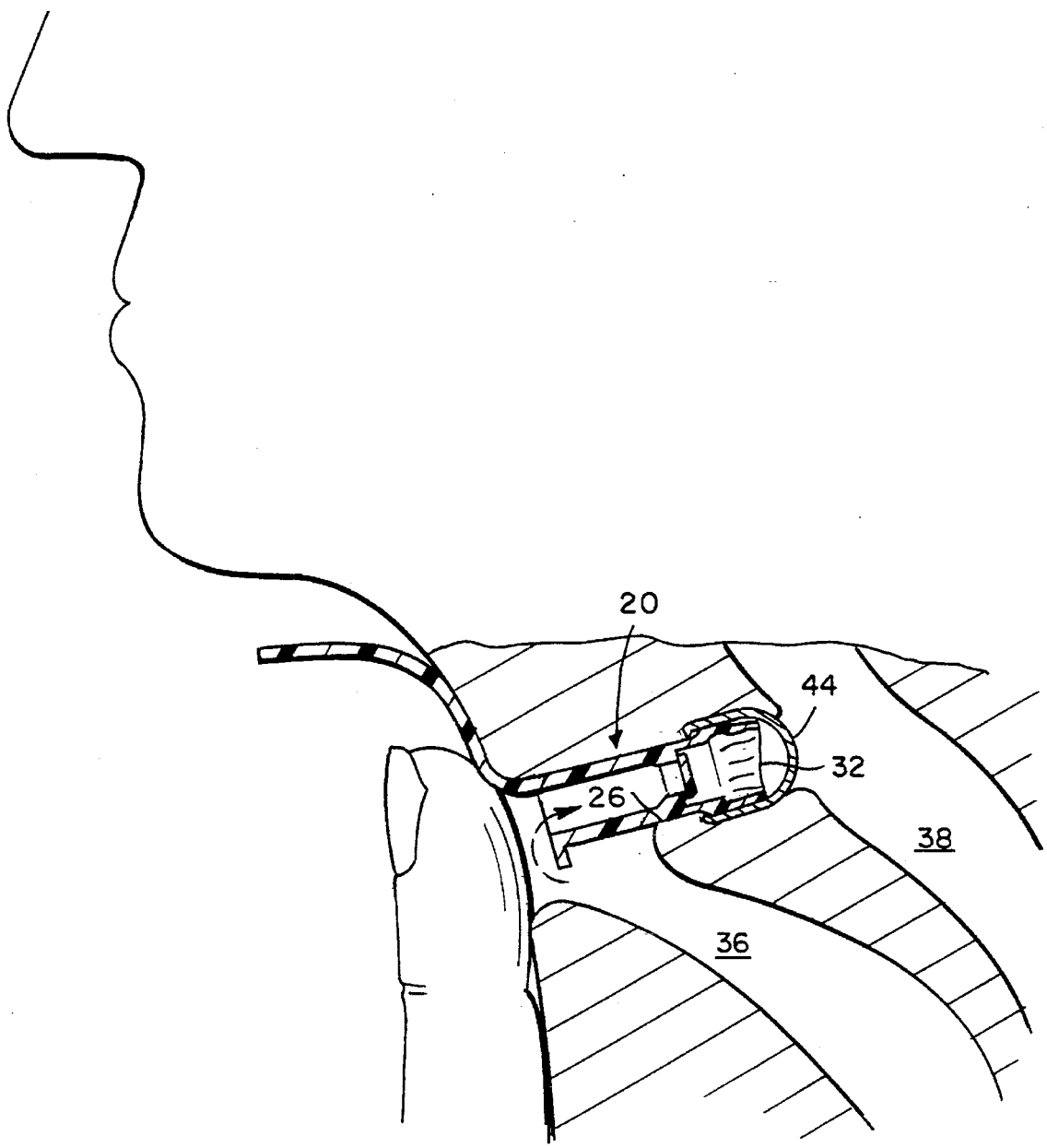
FIG. 11 illustrates a method for checking the placement of a speech prosthesis according to the present invention.

It is to be noted that if the insertion method, a step of which is described in connection with FIGS. 6–7 is employed, one test for proper deployment of the flange 32 is illustrated in FIG. 11. Namely, if the patient attempts to initiate esophageal speech through prosthesis 20 and too much force is required to get airflow through the prosthesis 20, that is an indication of incomplete deployment of the flange 32. This may mean that dissolution of the retainer 44 is incomplete and/or that the prosthesis 20 is too short to extend all the way through the puncture 26 from the tracheal end 36 to the esophageal end 38 thereof. This provides a convenient technique for use with the measuring probe which is used to measure the length of the puncture 26 between the trachea 36 and esophagus 38 to determine the correct length of prosthesis 20 for the patient.

FIGS. 12–13 illustrate steps of an alternative method to that described in connection with FIGS. 8–10 for the loading of a flange 30 or 32 into a retainer 44 or 144, to the orientation illustrated in FIGS. 2–4, 6 and 7. In the first step in the method, illustrated in FIG. 12, the prosthesis 20 is inserted into a tube 180. The outer sidewall 182 of tube 180 again can be knurled or otherwise textured to aid in gripping of the tube 180 during the process. Once the prosthesis has reached the orientation illustrated in FIG. 12, the retainer 44 or 144 is placed inside the end 184 of the tube 180. The inside 186 of end 184 is bevelled slightly to help in folding the flange 30 or 32 and to guide retainer 44 or 144 into the end 184 of tube 180. The retainer 44 or 144 is held in the end 184 of tube 180 as prosthesis 20 is pushed out of tube 180 into retainer 44 or 144 by, for example, the clinician's forefinger while a tool 88 is pushed through the tube 180 (FIG. 13), engages the open end of prosthesis 20 and pushes prosthesis 20 out of tube 180 carrying the retainer 44 or 144 with it to retain flange 30 or 32 in its folded orientation illustrated in FIGS. 2–4, 6–7, 9 or 10. The prosthesis 20 is then ready for insertion using one of the methods described in connection with FIGS. 2–4 and 6–7.

What is claimed is:

1. In combination, first and second tools, a device, and a retainer, the first tool for use in folding a resiliently foldable flexible flange of the device, the resiliently foldable flexible flange having a resiliently folded orientation and a deployed use orientation and in placing the retainer over the resiliently folded flexible flange of the device to retain the flange in its resiliently folded orientation, the device being for insertion into an opening in a wall of a human body, the retainer being constructed of a material soluble in fluids present adjacent the wall, the device having a cylindrical device body, the flexible flange provided on an outside surface of the device body, the first tool comprising a cylindrical passageway having a cross section slightly larger than a cross section of the device body but smaller than the flange, the passageway having an open end for receiving the device, the open end of the first tool provided with an edge, the edge of the open end causing the flange to be resiliently folded toward the device body as the device is inserted into the passageway, means for receiving the retainer at the open end, and the second tool for ejecting the device with the flange retained in its resiliently folded orientation by the retainer from the passageway through the open end.

2. The combination of claim 1 wherein the passageway is defined by an inner sidewall of a tube, the tube also having an outer sidewall, the means for receiving the retainer comprising the outer sidewall adjacent the open end of the passageway.

3. The combination of claim 1 wherein the passageway is defined by an inner sidewall of the tool, the open end and a region between the inner sidewall and the open end, the inner sidewall having an inner sidewall cross section, the open end having an open end cross section, and the region having a cross section increasing from the inner sidewall cross section to the open end cross section.

* * * * *